United States Patent [19]

Krämer et al.

[11] Patent Number: 4,632,932
[45] Date of Patent: * Dec. 30, 1986

[54] ANTIMYCOTIC AGENTS

[75] Inventors: Wolfgang Krämer, Wuppertal; Karl H. Büchel, Burscheid; Graham Holmwood; Erik Regel, both of Wuppertal; Manfred Plempel, Haan, all of Fed. Rep. of Germany

[73] Assignee: Bayer Aktiengesellschaft, Leverkusen, Fed. Rep. of Germany

[*] Notice: The portion of the term of this patent subsequent to Nov. 11, 2003 has been disclaimed.

[21] Appl. No.: 549,868

[22] Filed: Nov. 8, 1983

[30] Foreign Application Priority Data

Nov. 15, 1982 [DE] Fed. Rep. of Germany ....... 3242236

[51] Int. Cl.$^4$ .............................................. A61K 31/41
[52] U.S. Cl. ..................................... 514/383; 514/184; 514/399; 548/101; 548/262; 548/336

[58] Field of Search ................... 424/269, 245, 273 R; 514/184, 383, 399

[56] References Cited

U.S. PATENT DOCUMENTS 4,496,388 1/1985 Clough II ........................... 548/262

FOREIGN PATENT DOCUMENTS 0078594 5/1983 European Pat. Off. ............ 548/262
3018866 11/1981 Fed. Rep. of Germany ...... 548/262
3018865 11/1981 Fed. Rep. of Germany ...... 424/269

Primary Examiner—Richard L. Raymond
Attorney, Agent, or Firm—Sprung Horn Kramer & Woods

[57] ABSTRACT

The invention concerns the provision of compound of Formula I as defined herein as well as compositions containing compound of Formula I. Said compounds and compositions are used as antimycotic agents and the invention includes such use.

21 Claims, No Drawings

ANTIMYCOTIC AGENTS

The present invention relates to the use of new heterocyclically substituted hydroxyalkyl-azolyl derivatives as antimicrobial agents, in particular as antimycotics.

It has already been disclosed that certain 1-hydroyethyl-azolyl derivatives.

The new heterocyclically substituted hydroxyalkyl-azolyl derivatives of the formula (I)

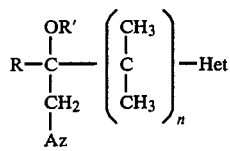

in which
Az represents 1,2,4-triazol-1-yl, 1,2,4-triazol-4-yl or imidazol-1-yl,
Het represents optionally substituted dioxolanyl or 1,3-dioxanyl,
R represents alkyl, optionally substituted phenyl, optionally substituted phenylalkyl, optionally substituted phenoxyalkyl, optionally substituted phenylthioalkyl, optionally substituted cycloalkyl, optionally substituted cycloalkyl, alkenyl, optionally substituted phenylalkenyl, optionally substituted cyclohexylalkenyl, furyl, naphthyloxymethyl or azolylalkyl,
R' represents hydrogen, optionally substituted alkyl or alkenyl and
n represents the numbers 0 or 1,
and their acid addition salts have been found. They possess good antimicrobial properties, in particular antimycotic properties, and can therefore be used as active compounds of antimycotic agents. The compounds of the formula (I) can possess an asymmetric carbon atom, and can therefore be obtained in the form of the two optical isomers as well as in racemic form.

Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

Surprisingly, the heterocyclically substituted hydroxyalkyl-azolyl derivatives to be used according to the invention, of the formula (I), exhibit a better antimycotic action spectrum, in particular better, therapeutically useful in vivo activity, than the compounds 1-(4-cchlorophenoxy)-3,3-dimethyl-2-(imidazol-1-yl-methyl)-2-butanol, 1-(2-methylphenoxy)-3,3-dimethyl-2-(imidazol-1-yl-methyl)- or -(1,2,4-triazol-1-yl-methyl)-2-butanol or 1-(2-methylphenyl)-4,4-dimethyl-3-(imidazol-1-yl-methyl)-3-pentanol, which are known from the state of the art and are similar compounds structurally and in terms of their action. The use, according to the invention, of the substances of the formula (I) thus represents an enrichment of medicine.

Formula (I) gives a general definition of the heterocyclically substituted hydroxyalkyl-azolyl derivatives according to the invention. In this formula,
Az preferably represents 1,2,4-triazol-1-yl, 1,2,4-triazol-4-yl or imidazol-1-yl;
Het preferably represents dioxolan-2-yl or 1,3-dioxanyl, each of which is optionally monosubstituted, disubstituted or polysubstituted by identical or different substituents, examples of substituents being: alkyl having 1 to 4 carbon atoms, and phenyl or phenoxyalkyl having 1 to 4 carbon atoms in the alkyl part, each of which is optinally monosubstituted, disubstituted or polysubstituted by identical or different substituents, examples of phenyl substituents being: halogen, alkyl having 1 to 4 carbon atoms, alkoxy and alkylthio, each having 1 or 2 carbon atoms, and halogenoalkyl, halogenoalkoxy and halogenoalkylthio each having 1 or 2 carbon atoms and 1 to 5 identical or different halogen atoms, such as, preferably, fluorine atoms or chlorine atoms;
R represents straight-chain or branched alkyl having 1 to 7 carbon atoms, or phenyl, phenylalkyl having 1 to 4 carbon atoms in the alkyl part, phenoxy- and phenylthioalkyl, each having 1 to 4 carbon atoms in the alkyl part, each of which is optionally monosubstituted, disubstituted or polysubstituted by identical or different substituents, and represents phenylethenyl, examples of substituents on the phenyl groups being: halogen, alkyl having 1 to 4 carbon atoms, alkoxy and alkylthio, each having 1 to 2 carbon atoms, nitro, halogenoalkyl and halogenoalkoxy and halogenoalkylthio, each having 1 or 2 carbon atoms and 1 to 5 identical or different halogen atoms, such as, preferably, fluorine atoms and chlorine atoms, hydroximinoalkyl having 1 to 4 carbon atoms, alkoximino-alkyl having 1 to 4 carbon atoms in each alkyl part, and phenyl, phenoxy, benzyl and benzyloxy, each of which is optionally substituted by halogen and alkyl having 1 to 4 carbon atoms; R furthermore preferably represents cycloalkyl having 5 to 7 carbon atoms, each of which is optionally monosubstituted, disubstituted or polysubstituted by identical or different alkyl radicals having 1 to 4 carbon atoms, or represents cycloalkylmethyl or -ethyl having 5 to 7 carbon atoms in the cycloalkyl part and cyclohexylethenyl; R additionally preferably represents alkenyl having 2 to 6 carbon atoms, -2 3-furyl, naphthyloxymethyl, 1,2,4-triazol-1-yl-methyl, imidazol-1-yl-methyl and pyrazol-1-yl-methyl;
R' preferably represents hydrogen, optionally phenyl-substituted alkyl having 1–4 carbon atoms, the phenyl radical being optionally substituted by the phenyl substituents mentioned in the case of R, and represents alkenyl having 2 to 4 carbon atoms; and
n preferably represents the numbers 0 or 1.

Particularly preferred compounds of the formula (I) are those in which

Az represents 1,2,4-triazol-1-yl, 1,2,4-triazol-4-yl or imidazol-1-yl;

Het represents dioxolan-2-yl, 1,3-dioxan-5-yl or 1,3-dioxan-2-yl, each of which is optionally monosubstituted; disubstituted or trisubstituted by identical or different substituents, examples of substituents being: methyl, ethyl, n-propyl, isopropyl, and phenyl and phenoxymethyl, each of which is optionally monosubstituted, disubstituted or trisubstituted by identical or different substituents from amongst fluorine, chlorine, methyl, trifluoromethyl or trifluoromethoxy;

R represents tert.-butyl, trimethyl-propyl, tetramethyl-propyl, and phenyl, benzyl, phenethyl, phenoxymethyl, phenylthiomethyl or phenethenyl, each of which is optionally monosubstituted, disubstituted or trisubstituted by identical or different substituents, examples of phenyl substituents being: fluorine, chlorine, methyl, trifluoromethyl, trifluoromethoxy, trifluoromethylthio, hydroximinomethyl, 1-hydroximinoethyl, methoximinomethyl and 1-methoximinoethyl, and phenyl, phenoxy or benzyl and benzyloxy, each of which is optionally substituted by chlorine and/or methyl; R furthermore represents cyclohexyl, cyclohexylmethyl, cyclohexylethyl or cyclohexylethenyl, each of which is optionally monosubstituted or disubstituted by identical or different substituents from amongst methyl, ethyl or isopropyl;

R furthermore represents allyl, dimethylpropenyl, 2-furyl, naphthyloxymethyl, 1,2,4-triazol-1-yl-methyl, 1,2,4-triazol-4-yl-methyl, imidazol-1-yl-methyl or pyrazol-1-yl-methyl, R' represents hydrogen, methyl, 4-chlorobenzyl or allyl, and n represents the number 0 or 1.

Preferred compounds according to the invention are also addition salts of an acid and those heterocyclically substituted hydroxyalkyl-azolyl derivatives of the formula (I) in which the substituents Az, Het, R and R' and the index n have the meaning which have already been mentioned as being preferred for the substituents and the index.

The acids with which addition salts can be formed preferably include hydrohalic acids, such as, for example, hydrochloric acid and hydrobromic acid, in particular hydrochloric acid, and also phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as sulphonic acids, such as, for example, p-toluenesulphonic acid and naphthalene-1,5-disulphonic acid.

In addition to the compounds mentioned in the illustrative preparation examples, the following compounds of the new formula (Ia) may be mentioned individually and are, of course, included in the invention:

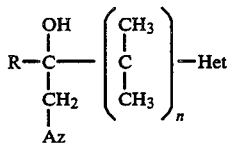

-continued $$R-\underset{\underset{Az}{\overset{\overset{OH}{|}}{\underset{|}{C}}}}{\overset{\overset{OH}{|}}{C}}-CH_2-\left(\underset{\underset{CH_3}{|}}{\overset{\overset{CH_3}{|}}{C}}\right)_n-Het \quad (Ia)$$

| R | Az | n | Het |
|---|---|---|---|
| 4-Cl-C₆H₄-CH=CH- | 1,2,4-triazol-1-yl | 1 | 2-ethyl-1,3-dioxolan-2-yl |
| 4-Cl-C₆H₄-CH₂-CH₂- | 1,2,4-triazol-1-yl | 1 | 2-ethyl-1,3-dioxolan-2-yl |
| 4-Cl-C₆H₄-O-CH₂- | 1,2,4-triazol-1-yl | 1 | 2-ethyl-1,3-dioxolan-2-yl |
| (1,2,4-triazol-1-yl)-CH₂- | 1,2,4-triazol-1-yl | 1 | 2-(2,4-dichlorophenoxymethyl)-1,3-dioxolan-2-yl |
| (1,2,4-triazol-1-yl)-CH₂- | 1,2,4-triazol-1-yl | 1 | 2-(4-chlorophenyl)-1,3-dioxolan-2-yl |
| 4-Cl-C₆H₄-S-CH₂- | 1,2,4-triazol-1-yl | 1 | 1,3-dioxolan-2-yl |
| 4-Cl-C₆H₄-CH₂- | 1,2,4-triazol-1-yl | 1 | 1,3-dioxolan-2-yl |
| 4-Cl-C₆H₄-CH₂-C(CH₃)₂- | 1,2,4-triazol-1-yl | 1 | 1,3-dioxolan-2-yl |
| 4-Cl-C₆H₄-OCH₂-C(CH₃)₂- | 1,2,4-triazol-1-yl | 1 | 1,3-dioxolan-2-yl |
| C₆H₁₁-CH=CH- | 1,2,4-triazol-1-yl | 1 | 2-ethyl-1,3-dioxolan-2-yl |
| C₆H₁₁-CH₂-CH₂- | 1,2,4-triazol-1-yl | 1 | 2-ethyl-1,3-dioxolan-2-yl |

-continued
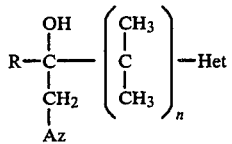
(Ia)
| R | Az | n | Het |
|---|---|---|---|
| (H3C)3C-C(CH3)2- | -N(triazole) | 1 | -O-CH(-O-CH2-C6H4-Cl)- |
| H3C=HC-C(CH3)2- | -N(triazole) | 1 | -O-CH(-O-CH2-C6H4-Cl)- |
| cyclohexyl-CH=CH- | -N(triazole) | 0 | H3C-C(CH3)(-O-)(-O-)C(CH3)2 |
| cyclohexyl-CH2-CH2- | -N(triazole) | 0 | H3C-C(CH3)(-O-)(-O-)C(CH3)2 |
| 2,4-Cl2-C6H3- | -N(triazole) | 1 | -O-CH(-O-C2H5)- |
| 3-CF3-C6H4- | -N(triazole) | 1 | -O-CH(-O-)- |
| H3CON=CH-C6H4-O-CH2- | -N(triazole) | 1 | -O-CH(-O-)- |
| H3CON=C(CH3)-C6H4-O-CH2- | -N(triazole) | 1 | -O-CH(-O-)- |
| 2,4-Cl2-C6H3- | -N(imidazole) | 0 | -O-CH(-O-C2H5)- |
| 2,4-Cl2-C6H3- | -N(triazole) | 0 | -O-CH(-O-C2H5)- |

The heterocyclically substituted hydroxyalkylazolyl derivatives, their ether and ester derivatives and their acid addition salts of the invention are not yet known. However, they can be prepared by methods in which
(a) an oxirane of the formula (II)

$$R-\underset{O\underset{\diagdown}{-}CH_2}{\overset{\diagup}{C}}-\left(\begin{array}{c}CH_3\\|\\C\\|\\CH_3\end{array}\right)_n-Het \quad (II)$$

in which
Het, R and n have the meaning given above, is reacted with an azole of the formula (III)

$$M-Az \quad (III)$$

in which
Az has the meaning given above and
M represents hydrogen or an alkali metal salt, in the presence of an inert organic solvent, such as, for example, an alcohol (particularly 2 $C_1$-$C_3$-alkanol), and if appropriate in the presence of a base, such as, for example, a sodium alcoholate or potassium hydroxide, at temperatures between 60° C. and 150° C.; or
(b) an azoloketone of the formula (IV)

$$Az-CH_2-CO-\left(\begin{array}{c}CH_3\\|\\C\\|\\CH_3\end{array}\right)_n-Het \quad (IV)$$

in which
Az, Het and n having the meaning given above, or reacted with an organo-magnesium compound of the formula (V)

$$R-Mg-X \quad (V)$$

in which
R has the meaning given above and
X represents chlorine, bromine or iodine, in the presence of a diluent, such as, for example, an ether (such as a $C_1$-$C_2$-dialkyl ether), at a temperature between 30° C. and 80° C.; or
(c) an azolo-oxirane of the formula (VI)

$$Az-CH_2-\underset{O\underset{\diagdown}{-}CH_2}{\overset{\diagup}{C}}-\left(\begin{array}{c}CH_3\\|\\C\\|\\CH_3\end{array}\right)_n-Het \quad (VI)$$

in which
R has the meaning given above and
Me represents an alkali metal or —Mg—X, wherein
X has the meaning given above, is converted under the conditions of process (a), and furthermore, if appropriate,
(d) a hydroxy compound which is prepared according to process (a), (b) or (c) and in which R' in formula (I) represents hydrogen, is converted, in the presence of a diluent, to the alkali metal alcoholate, and the latter is reacted with a halide to give the corresponding ether derivative in which R' in formula (I) represents optionally substituted alkyl or phenyl.

In addition, the resulting compounds of the formula (I) or their ethers can, if appropriate, then be subjected to an addition reaction with an acid.

The oxiranes of the formula (II) are not yet known. However, they can be prepared in a generally known manner by a method in which a ketone of the formula (VIII)

$$R-CO-\left(\begin{array}{c}CH_3\\|\\C\\|\\CH_3\end{array}\right)_n-Het \quad (VIII)$$

in which
Het, R and n have the meaning given above, is either
(α) reacted with dimethyloxosulphonium methylide of the formula (IX)

$$\overset{\delta+}{(CH_3)_2SO}\overset{\delta-}{CH_2} \quad (IX)$$

in a manner which is in itself known, in the presence of a diluent, such as, for example, dimethylsulphoxide, at a temperature between 20° C. and 80° C. (in this context, see J. Am. Chem. Soc. 87, 1368–1364 (1965)), or
(β) reacted with trimethylsulphonium methylsulphate of the formula (X)

$$[(CH_3)_3S^{(+)}]CH_3SO_4^{(-)} \quad (X)$$

in a manner which is in itself known, in the presence of an inert organic solvent, such as, for example, acetonitrile, and in the presence of a base, such as, for example, sodium methylate, at a temperature between 0° C. and 60° C., preferably at room temperature (see also Heterocycles 8, 397 (1977)).

The resulting oxiranes of the formula (III) can, if appropriate, be directly reacted further, without being isolated.

Some of the ketones, of the formula (VIII) in which n=1, which are required as starting materials in the preparation of the oxiranes of the formula (II) are known (see, for example, J. Org. Chem. 32, 404 (1967)), or they form the subject of the prior patent applications of the Applicant, which applications have not yet been published (see the German Patent Applications No. P 32 24 130 of 29/6/1982 corresponding to U.S. Ser. No. 503,102 of 10/6/83 and No. P 32 24 129 of 29/6/82 corresponding to U.S. Ser. No. 503,220 of 10/6/83, they can be obtained in a known manner, by a method in which 1-(n-morpholino)-isobutene of the formula (XI)

$$O\diagup\overline{\phantom{N}}\diagdown N-CH=C(CH_3)_2 \quad (XI)$$

is reacted with a chloride of the formula (XII)

$$R-CO-Cl \quad (XII)$$

in which

R has the meaning given above, in the presence of a solvent, such as, for example, diethyl ether, at a temperature between 20° C. and 120° C., and the resulting keto derivative of the formula (XIII)

in which
R has the meaning given above,
are transformed into derivatives in a conventional manner at the aldehyde group with appropriate diols, in the presence of an inert organic solvents, such as, for example, toluene, and in the presence of a strong acid as catalyst, such as, for example, p-toluenesulphonic acid, at temperatures between 80° C. and 110° C.

Some of the ketones, of the formula (VIII) in which $n=0$, which are required as starting materials in the preparation of the oxiranes of the formula (II) are known (see, for example, EP-OS (European Published Specification) No. 0,043,923), or they can be obtained in a known manner by a method in which aldehyde-ketones (see, for example, Houben-Weyl, Methoden der organischen Chemie (Methods of organic chemistry), Volume 7/1, page 185) of the formula (XIV)

in which
R has the meaning given above, or their acetals or their ketals of the formula R—C(OCH$_3$)$_2$—CHO (for the preparation, see Bull. Soc. Chim. France, 1971, page 2598) are reacted in a conventional manner, at the aldehyde group, with appropriate diols, in the presence of an inert organic solvent, such as, for example, toluene, and in the presence of a strong acid, such as, for example, p-toluenesulphonic acid, at temperatures between 40° C. and 110° C.

Ketones of the formula (VIII) in which R=optionally substituted phenethyl or cyclohexylethenyl can also be obtained by subjecting appropriate benzyldehydes or cyclohexylcarbaldehydes to an aldol condensation with appropriate methyl ketones in a conventional manner. The resulting ketones of the formula (VIII) in which R=optionally substituted phenethenyl or cyclohexylethenyl can, if required, be hydrogenated in a conventional to give ketones of the formula (VIII) in which R=optionally substituted phenethyl or cyclohexylethyl (see also the preparation examples).

The dimethyloxosulphonium methylide of the formula (IX) required in process variant (α) is likewise known (see J. Amer. Chem. Soc. 87, 1363–1364 (1965)). In the above reaction, it is processed in a freshly prepared state by producing it in situ by reacting trimethyloxosulphonium iodide with sodium hydride or sodium amide in the presence of a diluent.

The trimethylsulphonium methylsulphate of the formula (X) required in process variant (β) is likewise known (see Heterocycles 8, 397 (1977)). In the above reaction, it is likewise employed in a freshly prepared state by producing it in situ by reacting dimethyl sulphide with dimethyl sulphate.

The azoles of the formula (III) are generally known compounds of organic chemistry.

Some of the azoloketones of the formula (IV) are knwon (see, for example, EP-OS (European Published Specification) No. 0,043,923), but some of them form the subject of a prior patent application of the Applicant, which application has not yet been published (see the German Patent Application No. P 32 24 129 of 29/6/1982). The azoloketones of the formula (IV) can be obtained in a generally known manner by a method in which halogenomethyl-ketones of the formula (XV)

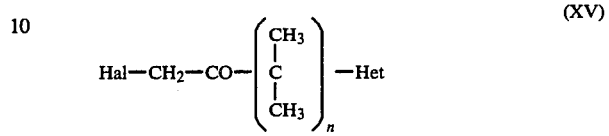

in which
Het and n have the meaning given above and
Hal represents chlorine or bromine,
are reacted in a conventional manner with 1,2,4-triazole or imidazole, in the presence of an inert organic solvent, such as, for example, acetone, and in the presence of an acid-binding agent, such as, for example, potassium carbonate, at temperatures between 20° C. and 150° C.

The halogenomethyl-ketones, of the formula (XV) in which $n=1$, which are required as starting materials for the preparation of the azoloketones of the formula (IV) are not yet known; they, too, form the subject of a prior patent applicatin of the Applicant, which application has not yet been published (see the German Patent Application No. P 32 24 129 of 29/6/1982). They can be obtained in accordance with the preparation, described above, of the ketones of the formula (VIII) in which $n=1$.

Some of the halogenomethyl-ketones, of the formula (XV) in which $n=0$, which are required as starting materials in the preparation of the azoloketones of the formula (IV) are known (see EP-OS (European Published Specification) No. 0,043,923)); they can be obtained, for example, in a known manner, by halogenation, as, for example, with N-bromosuccinimide, of appropriate ketones of the formula (VIII).

The organo-magnesium compounds of the formula (V) are generally known compounds of organic chemistry; or they are obtained in a generally known manner.

The azolo-oxiranes of the formula (VI) are not yet known; however, they can be obtained in a generally known manner by epoxidising azoloketones of the formula (IV) in accordance with process variants (α) and (β) indicated above.

The phenols and thiophenols and the metal-containing compounds of the formula (VII) are generally known compounds of organic chemistry.

To prepare the ethers of the compounds of the formula (I), the following procedure is advantageously followed: compounds of the formula (I), in a suitable inert organic solvent, are converted, by means of an alkali metal hydride or amide, into the alkali metal alcoholate, and the latter, without being isolated, is immediately reacted with an appropriate halide, such as, in particular, an alkyl halide, the ethers of the compounds of the formula (I) being obtained in one operation, with elimination of alkali metal halide.

In a preferred embodiment, the preparation of the alcoholates and their further reaction with a halide are advantageously carried out in a two-phase system, such as, for example, aqueous sodium hydroxide or potassium hydroxide solution/toluene or methylene chloride, with the addition of 0.01 to 1 mol of a phase-transfer catalyst such as, for example, ammonium or phosphonium compounds, and the alcoholates are formed in the organic phase or at the boundary, and are reacted with the halides present in the organic phase.

The hydroxy compounds which are obtainable by processes (a), (b) and (c) according to the invention and in which R' in formula (I) represents hydrogen can also be converted to the corresponding esters.

To prepare the esters, the following procedure is advantageously followed: compounds of the formula (I) are reacted, for example, with acid halides in the presence of an inert organic solvent, such as, for example, ethyl acetate, at temperatures between 0° C. and 100° C.; or with acid anhydrides in the presence of an inert organic solvent, such as, for example, methylene chloride or an excess of the acid anhydride, and in the presence of a catalyst, such as, for example, sodium acetate, at temperatures between 0° C. and 150° C.

The compounds of the formula (I) and their esters can also be converted to acid addition salts.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

The compounds of the formula (I) of the invention, their ester derivatives and their acid addition salts, display antimicrobial action, in particular powerful antimycotic action. They possess a very broad antimycotic action spectrum, especially against dermatophytes and blastomyces as well as biphase fungi, for example against varieties of Candida, such as Candida albicans, varieties of Epidermophytes, such as Epidermophyton floccosum; varieties of Aspergillus, such as Aspergillus niger and Aspergillus fumigatus, varieties of Trichophyton, such as Trichophyton mentagrophytes, varieties of Microsporon, such as Microsporon felineum and varieties of Torulospsis, such as Torulospsis glabrata. The listing of these micro-organisms in no way implies a limitation of the germs which can be combated but is only of illustrative character.

Examples which may be mentioned of fields of indication in medicine are: dermatomycoses and systemic mycoses caused by Trichophyton mentagrophytes and other varieties of Trichophyton, varieties of Microsporon, Epidermophyton floccosum, blastomyces and biphase fungi as well as moulds.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in human and veterinary medicine, for the prevention, alleviation and/or cure of the abovementioned diseases.

The active compounds or the pharmaceutical formulations can be administered locally, orally, parenterally, intraperitoneally and/or rectally, preferably parenterally, and in particular intravenously.

In general, it has proved advantageous in medicine, to administer the active compound or compounds according to the invention in total amounts of about 10 to about 300, preferably 50 to 200, mg/kg of body weight every 24 hours, optionally in the form of several individual administrations, in order to achieve the desired results. The administration can be orally, parenterally or topically. However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum dosage required and the type of administration of the active compound can easily be determined by anyone skilled in the art on the basis of his expert knowledge.

PREPARATION EXAMPLES

Example 1

(Process a)

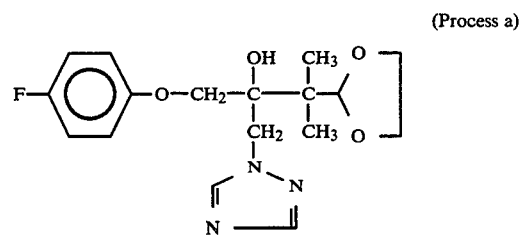

A solution of 17.6 g (0.0623 mol) of 2-[2-(1,3-dioxolan-2-yl)-prop-2-yl]-2-(4-fluorophenoxymethyl)-oxirane in 30 ml of n-propanol is added dropwise, at room temperature, to a solution of 4.93 g (0.0715 mol ) of 1,2,4-triazol and 0.36 g (0.0065 mol) of potassium hydroxide in 30 ml of n-propanol. The reaction mixture is heated under reflux for 2 days and then evaporated down. The residue is taken up in ethyl acetate, and the solution is washed twice with water and once with saturated sodium chloride solution, dried over sodium sulphate and evaporated down. The residue is purified by column chromatography (dichloromethane/ethyl acetate=3:1) and recrystallised from a small amount of ether.

10.2 g (47% of theory) of 3-(1,3-dioxolan-2-yl)-1-(4-fluorophenoxy)-3-methyl-2-(1,2,4-triazol-1-yl-methyl)-2-butanol of melting point 102° C. to 104° C. are obtained.

Preparation of the starting material

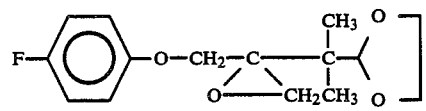

8.4 g (0.0748 mol) of potassium tert.-butylate are added to a suspension of 16.47 g (0.0748 mol) of trimethylsulphoxonium iodide in 20 ml of absolute dimethylsulphoxide at room temperature. The mixture is stirred for a further 30 minutes, and a solution of 3-(1,3-dioxolan-2-yl)-1-(4-fluorophenoxy)-3-methyl-butan-2-one in 20 ml of absolute toluene is then added dropwise. The reaction mixture is stirred overnight at room temperature, then heated for 2 hours at 50° C. and cooled, and water and toluene are added. The toluene phase is separated off, washed twice with water and once with saturated sodium chloride solution, dried over sodium sulphate and evaporated down.

17.6 g (91% of theory) of 2-[2-(1,3-dioxolan-2-yl)-pro-2-yl]-2-(4-fluorophenoxymethyl)-oxirane are obtained as an oil, which is directly reacted further.

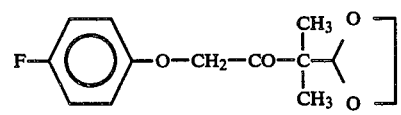

A mixture of 16.7 g (0.15 mol) of 4-fluorophenol, 29 g (0.15 mol) of 1-chloro-3-(1,3-dioxolan-2-yl)-3-methylbutan-2-one and 23.4 g (0.17 mol) of powdered potassium carbonate in 300 ml of methyl ethyl ketone is heated under reflux for 16 hours. The mixture is allowed to cool and filtered. The filtrate is evaporated down, the residue is taken up with dichloromethane, the solution is washed once with 5% strength sodium hydroxide solution and once with water, dried over sodium sulphate and evaporated down, and the residue is distilled. 29 g (72% of theory) of 3-(1,3-dioxolan-2-yl)-1-(4-fluorophenoxy)-3-methylbutan-2-one of boiling point 143° C. to 145° C./0.1 mbar are obtained.

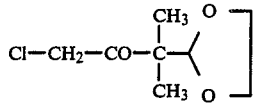

204 g (1.38 mol) of 4-chloro-2,2-dimethyl-3-ketobutanal are heated with 93 g (1.5 mol) of ethylene glycol and 0.7 g of p-toluenesulphonic acid in 400 ml of methylene chloride for 3 hours in a water separator. The organic phase is extracted with 150 ml of 5% strength sodium hydroxide solution and then with 400 ml of water. The solvent is distilled off and the residue is distilled in the vacuum from a water jet.

211 g (79.8% of theory) of 1-chloro-3-(dioxolan-2-yl-3-methylbutan-2-one of boiling point 127° C. to 128° C./14 mbar are obtained.

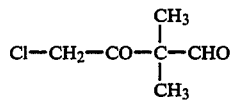

210 g (1.5 mol) of 1-(N-morpholino)-isobutene are added dropwise, in the course of one hour at 5° C., to 169 g (1.5 mol) of chloroacetyl chloride, dissolved in 350 ml of diethyl ether. When the addition is complete, the mixture is stirred for a further 3 hours under reflux. The solution is poured onto 100 g of ice and brought to pH 5 with aqueous sodium bicarbonate solution, and the ether phase is separated off. The aqueous phase is extracted with 100 ml of diethyl ether, the organic phases are combined and dried over sodium sulphate, the solvent is distilled off and the residue is distilled under the vacuum from a water jet.

136.4 g (61% of theory) of 4-chloro-2,2-dimethyl-3-ketobutanal of boiling point 95° C. to 98° C./14 mbar are obtained.

Example 2 and 3

(Process a)

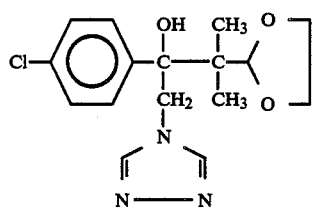

(Example 2)

-continued

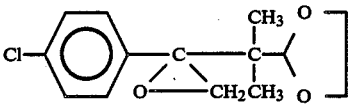

(Example 3)

A solution of 26.8 g (0.1 mol) of 2-(4-chlorophenyl)-2-[2-(1,3-dioxolan-2-yl)-prop-2-yl]-oxirane, 7.6 g (0.11 mol) of 1,2,4-triazole and 0.5 g of potassium hydroxide in 200 ml of absolute butanol is heated under reflux for 18 hours. The mixture is allowed to cool to room temperature, and 800 ml of water are added. The organic phase is separated off, dried over sodium sulphate and evaporated down. The residue is stirred with 200 ml of isopropyl ether/ethyl acetate (10:1).

The precipitated solid is filtered off and dried. 4.5 g (13.3% of theory) of 3-(1,3-dioxolan-2-yl)-2-(4-chlorophenyl)-3-methyl-1-(1,2,4-triazol-4-yl)-butan-2-ol (Example 2) of melting point 180° C. to 182° C. are obtained.

The filtrate is evaporated down and the residue is first taken up with 350 ml of acetone, after which 8 g of naphthalene-1,5-disulphonic acid in 30 ml of acetone are added. The mixture is stirred for 6 hours at 0° C., the solid is filtered off under suction and saturated aqueous sodium bicarbonate/methylene solution is added. The organic phase is separated off, dried over sodium sulphate and evaporated down.

19 g (56.2% of theory) of 3-(1,3-dioxolan-2-yl)-2-(4-chlorophenyl)-3-methyl-1-(1,2,4-triazol-1-yl)-butan-2-ol (Example 3) are obtained as an oil.

Preparation of the starting material

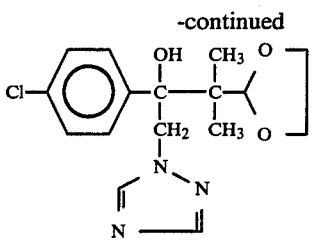

29.5 g (0.208 mol) of methyl iodide are added dropwise to 13.7 g (0.22 mol) of dimethyl sulphide in 130 ml of absolute dimethyl sulphoxide and 120 ml of absolute tetrahydrofuran, the temperature increasing to approx. 30° C. The mixture is stirred for a further 5 hours, and a solution of 33 g (0.13 mol) of 4-chlorophenyl 2-[2-(1,3-dioxolan-2-yl)-prop-2-yl]ketone in 100 ml of absolute toluene is then added. 9.5 g of sodium methylate are added in portions in the course of one hour. The reaction mixture is stirred for a further 3 hours, and a further 5.6 g of sodium methylate are added in two portions in the course of 30 minutes. The reaction mixture is stirred overnight and poured onto 700 ml of ice water. The organic phase is separated off and the aqueous phase is extracted by shaking with 200 ml of toluene. The combined organic phases are washed with twice 1,000 ml of water, dried over sodium sulphate and evaporated down. The oily residue is degassed in vacuo.

26.8 g of 2-(4-chlorophenyl)-2-[2-(1,3-dioxolan-2-yl)-prop-2-yl]-oxirane are obtained as an oil, which is directly reacted further.

Example 4

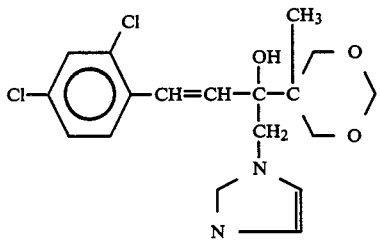

13.6 g (0.2 mol) of imidazole are added in portions to 6 g (80% strength, 0.2 mol) of sodium hydride in 200 ml of absolute dimethylformamide, the temperature increasing to approx. 45° C. The mixture is stirred for a further 30 minutes, and 34 g (0.108 mol) of 2-(2,4-dichlorophenethenyl)-2-(5-methyl-1,3-dioxan-5-yl)-oxirane in 50 ml of absolute dimethylformamide are then added. The reaction mixture is stirred for 4 hours at 80° C. It is cooled, and poured onto 800 ml of ice water/600 ml of methylene chloride. The mixture is stirred for a further 45 minutes, and the methylene chloride phase is separated off, washed twice with water, dried over sodium sulphate and evaporated down. The residue is recrystallised from ether.

10.5 g (25.4% of theory) of 1-(2,4-dichlorophenyl)-4-(imidazol-1-yl)-3-(5-methyl-1,3-dioxan-5-yl)-but-1-en-3-ol of melting point 142° C. to 144° C. are obtained.

Preparation of the starting material

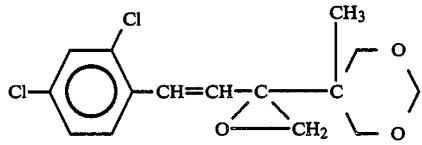

56.8 g (0.4 mol) of methyl iodide are added dropwise to 26.4 g (0.425 mol) of dimethyl sulphide in 180 ml of absolute dimethylsulphoxide and 175 ml of absolute tetrahydrofuran, the temperature increasing to approx. 35° C. The mixture is stirred for a further 16 hours, and a solution of 75.2 g (0.25 mol) of 2,4-dichlorophenethenyl 5-methyl-1,3-dioxan-5-yl ketone in 200 ml of absolute toluene is then added. 17.4 g (0.3 mol) of sodium methylate are then introduced in portions at 0° C. Stirring is continued for a further 3 hours, a further 10.8 g (0.2 mol) of sodium methylate are added and the mixture is stirred overnight. 250 ml of water are added to the reaction mixture, the toluene phase is separated off and the aqueous phase is extracted with twice 150 ml of toluene. The combined toluene phases are washed with three times 700 ml of water, dried over sodium sulphate and evaporated down. The oily residue is degassed in vacuo.

69 g of 2-(2,4-dichlorophenethenyl)-2-(5-methyl-1,3-dioxan-5-yl)-oxirane are obtained as an oil, which is directly reacted further.

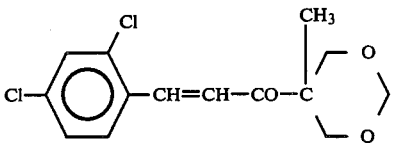

35 ml of 10% strength sodium hydroxide solution are added dropwise to 70 g (0.4 mol) of 2,4-dichlorobenzaldehyde and 57.5 g (85% strength, 0.4 mol) of methyl 5-methyl-1,3-dioxan-5-yl ketone in 140 ml of ethanol and 50 ml of water. The reaction mixture is stirred for a further 8 hours at room temperature, and is then poured onto 400 ml of methylene chloride. The organic phase is separated off, washed with water, dried over sodium sulphate and evaporated down. The oily residue crystallises after trituration with ether.

80 g of 2,4-dichlorophenethenyl 5-methyl-1,3-dioxan-5-yl ketone of melting point 100° C. to 102° C. are obtained.

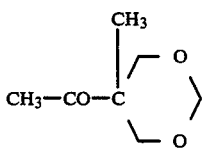

360 g (5 mol) of methyl ethyl ketone and 225 g (2.5 mol) of trioxane in 1,000 ml of chloroform are heated under reflux for 2 hours, 40 ml of concentrated sulphuric acid being added. The mixture is allowed to cool, 2 liters of water are added and stirring is continued for a further 10 minutes. The organic phase is separated off and stirred into saturated aqueous sodium bicarbonate solution, and the mixture is again stirred for 10 minutes. The organic phase is separated off, dried over sodium sulphate and evaporated down. The residue is distilled in vacuo.

199 g of methyl 5-methyl-1,3-dioxan-5-yl ketone of boiling point 50° C. to 52° C./0.8 mbar are obtained.

Example 5

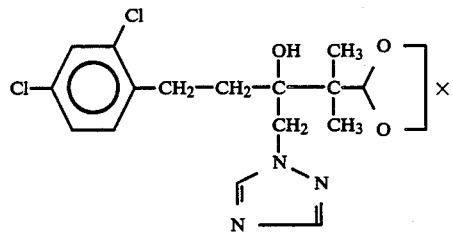

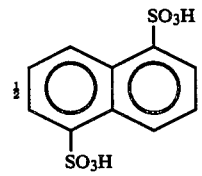

(Process a/salt formation)

13.8 g (0.2 mol) of 1,2,4-triazole are added in portions to a suspension of 6 g (80% strength, 0.2 mol) of sodium hydride in 330 ml of absolute dimethylformamide. The mixture is stirred for a further 30 minutes, and 2-(2,4- dichlorophenylethyl)-2-[2-(1,3-dioxolan-2-yl)-prop-2-yl]-oxirane in 80 ml of dimethylformamide is then added. The reaction mixture is stirred for 4 hours at 80° C. Thereafter, it is allowed to cool and poured onto 600 ml ice water/800 ml methylene chloride. The methylene chloride phase is separated off, washed with twice 1,500 ml of water, dried over sodium sulphate and evaporated down. The oily residue is taken up in 400 ml of acetone, and 14.4 g of naphthalene-1,5-disulphonic acid in 40 ml of acetone are added at 0° C. Stirring is continued for 5 hours, and the resulting precipitate is filtered off under suction.

43.1 g (29.1% of theory) of 1-(2,4-dichlorophenyl)-4-(1,3-dioxolan-2-yl)-4-methyl-3-(1,2,4-triazol-1-yl-methyl)-pentan-3-ol naphthalene-1,5-disulphonate of melting point 183° C. are obtained.

Preparation of the starting material

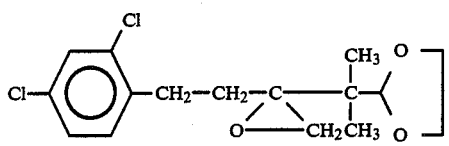

In accordance with Example 3, reaction of 83 g (0.262 mol) of b 2,4-dichlorophenylethyl 2-(1,3-dioxolan-2-yl)-prop-2-yl ketone with 28.2 g (0.455 mol) of dimethyl sulphide/60 g of methyl iodide gives 90 g of 2-(2,4-dichlorophenylethyl)-2-[2-(1,3-dioxolan-2-yl)-prop-2-yl]-oxirane as an oil, which is directly reacted further.

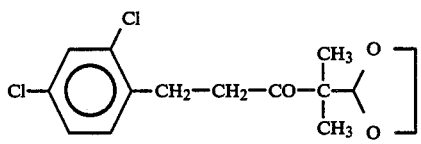

100 g of 2,4-dichlorophenylethenyl 2-(1,3-dioxolan-2-yl)-prop-2-yl)ketone are heated with 10 g of Raney nickel in 600 ml of tetrahydrofuran for 25 minutes under a pressure of 55 bar and at 25° C. The reaction mixture is then evaporated down, and the residue is distilled in vacuo.

83 g of 2,4-dichlorophenylethyl 2-(1,3-dioxolan-2-yl)-prop-2-yl ketone of boiling point 148° C./0.1 mbar are obtained.

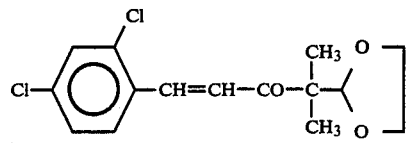

95 ml of 10% strength sodium hydroxide solution are added dropwise to 196 g (1.12 mol) of 2,4-dichlorobenzaldehyde and 178 g (0.125 mol) of methyl 2-(1,3-dioxolan-2-yl)-prop-2-yl ketone in 400 ml of ethanol and 140 ml of water. The reaction mixture is stirred for a further 10 hours, and the resulting solid is filtered off under suction and washed with ethanol.

309 g of 2,4-dichlorophenylethenyl 2-(1,3-dioxolan-2-yl)-prop-2-yl ketone of melting point 92° C. to 93° C. are obtained.

Example 6

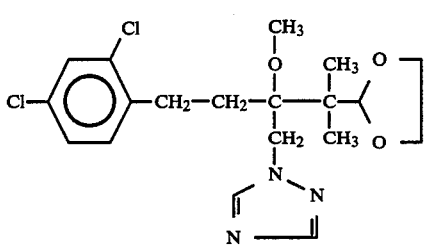

1.4 g (0.046 mol) of sodium hydride are added to 18 g (0.045 mol) of 1-(2,4-dichlorophenyl)-4-(1,3-dioxan-2-yl)-4-methyl-3-(1,2,4-triazol-1-yl-methyl)-pentan-3-ol in 150 ml of absolute dioxane. The mixture is stirred for a further 5 hours at room temperature, and 7.1 g (0.05 mol) of methyl iodide are added. Thereafter, stirring is continued overnight, and a further 0.7 g (0.023 mol) of sodium hydride and 3.5 g (0.025 mol) of methyl iodide are added. After the mixture has been stirred once again, it is evaporated down, the oily residue is taken up in methylene chloride and the solution is rinsed with twice 600 ml of water, dried over sodium sulphate and evaporated down. The residue is recrystallised from isopropyl ether.

12 g (64.4% of theory) of 1-(2,4-dichlorophenyl)-4-(1,3-dioxan-2-yl)-3-methoxy-4-methyl-3-(1,2,4-triazol-1-yl-methyl)-pentane of melting point 130° C. to 132° C. are obtained.

The following compounds of the formula (Ia) are obtained in an analogous manner and in accordance with the process data according to the invention:

(Ia)

$$R-\underset{\underset{Az}{|}}{\overset{\overset{OH}{|}}{C}}-\left(\underset{\overset{|}{CH_3}}{\overset{\overset{CH_3}{|}}{C}}\right)_n-Het$$

| Example No. | R | Az | n | Het | Melting point (°C.) or $n_D^{20}$ |
|---|---|---|---|---|---|
| 7 | Cl-⌬-CH₂—CH₂— | triazolyl | 1 | 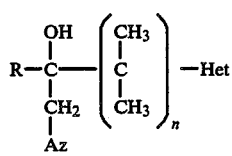 | 179 (X ½ NDA) |

-continued (Ia)

$$R-\underset{\underset{Az}{|}}{\overset{\overset{OH}{|}}{C}}-CH_2-\left(\underset{CH_3}{\overset{CH_3}{\underset{|}{\overset{|}{C}}}}\right)_n-Het$$

| Example No. | R | Az | n | Het | Melting point (°C.) or $n_D^{20}$ |
|---|---|---|---|---|---|
| 8 | 2,4-Cl₂-C₆H₃-CH₂-CH₂- | 1,2,4-triazol-1-yl | 0 | 2-methyl-1,3-dioxolan-2-yl (CH₃, O, O) | 119–121 |
| 9 | 4-Cl-C₆H₄-CH₂-CH₂- | 1,2,4-triazol-1-yl | 0 | 2-methyl-1,3-dioxolan-2-yl | 125–127 |
| 10 | 4-Cl-C₆H₄-CH=CH- | 1,2,4-triazol-1-yl | 1 | 1,3-dioxolan-2-yl | 116–118 |
| 11 | 2,4-Cl₂-C₆H₃-CH=CH- | 1,2,4-triazol-1-yl | 1 | 1,3-dioxolan-2-yl | 93 |
| 12 | 4-Cl-C₆H₄-CH=CH- | 1,2,4-triazol-1-yl | 0 | 2-methyl-1,3-dioxolan-2-yl | 182–184 |
| 13 | 4-Cl-C₆H₄-CH=CH- | 1,2,4-triazol-1-yl | 0 | 2-methyl-1,3-dioxolan-2-yl | 171–173 |
| 14 | 4-biphenyl-O-CH₂- | 1,2,4-triazol-1-yl | 1 | 1,3-dioxolan-2-yl | 106–107 |
| 15 | 4-Cl-C₆H₄-O-CH₂- | 1,2,4-triazol-1-yl | 1 | 1,3-dioxolan-2-yl | 105–107 |
| 16 | 4-Cl-C₆H₄-O-CH₂- | 1,2,4-triazol-1-yl | 0 | 2-methyl-1,3-dioxolan-2-yl | 102–107 |
| 17 | 2,4-Cl₂-C₆H₃-O-CH₂- | 1,2,4-triazol-1-yl | 0 | 2-methyl-1,3-dioxolan-2-yl | 117–122 |
| 18 | 4-Cl-C₆H₄-O-CH₂- | imidazol-1-yl | 0 | 2-methyl-1,3-dioxolan-2-yl | 220–225 |

-continued $$R-\underset{\underset{Az}{|}}{\overset{\overset{OH}{|}}{\underset{|}{C}}}-CH_2-\left(\underset{\underset{CH_3}{|}}{\overset{\overset{CH_3}{|}}{C}}\right)_n-Het \qquad (Ia)$$

| Example No. | R | Az | n | Het | Melting point (°C.) or $n_D^{20}$ |
|---|---|---|---|---|---|
| 19 | 4-Cl-C$_6$H$_4$-CH$_2$-CH$_2$- | -N(imidazolyl) | 1 | 1,3-dioxolan-2-yl | 93 |
| 20 | 2,4-Cl$_2$-C$_6$H$_3$-CH$_2$-CH$_2$- | -N(imidazolyl) | 1 | 1,3-dioxolan-2-yl | 140–143 (× ½ NDA) |
| 21 | 2,4-Cl$_2$-C$_6$H$_3$-CH$_2$-CH$_2$- | -N(imidazolyl) | 0 | 5-CH$_3$-1,3-dioxan-2-yl | 122–124 |
| 22 | 4-Cl-C$_6$H$_4$-CH$_2$-CH$_2$- | -N(imidazolyl) | 0 | 5-CH$_3$-1,3-dioxan-2-yl | 68–73 |
| 23 | 4-Cl-C$_6$H$_4$-CH=CH- | -N(imidazolyl) | 1 | 1,3-dioxolan-2-yl | 164–166 |
| 24 | 2,4-Cl$_2$-C$_6$H$_3$-CH=CH- | -N(imidazolyl) | 1 | 1,3-dioxolan-2-yl | 122–125 |
| 25 | 4-Cl-C$_6$H$_4$-CH=CH- | -N(imidazolyl) | 0 | 5-CH$_3$-1,3-dioxan-2-yl | 192–195 |
| 26 | 4-Cl-C$_6$H$_4$-O-CH$_2$- | -N(imidazolyl) | 0 | 5-CH$_3$-1,3-dioxan-2-yl | 141–144 |
| 27 | 2,4-Cl$_2$-C$_6$H$_3$-O-CH$_2$- | -N(imidazolyl) | 0 | 5-CH$_3$-1,3-dioxan-2-yl | 176–177 |
| 28 | (1,2,4-triazol-1-yl)-CH$_2$- | -N(imidazolyl) | 1 | 1,3-dioxolan-2-yl | 1,5240 |
| 29 | 4-biphenylyl-O-CH$_2$- | -N(imidazolyl) | 1 | 4-C$_2$H$_5$-1,3-dioxolan-2-yl | 89–92 |

-continued $$R-\underset{\underset{Az}{\overset{OH}{\overset{|}{C}}}-\underset{CH_2}{\overset{|}{|}}}{\overset{|}{C}}\left(\underset{CH_3}{\overset{CH_3}{\overset{|}{C}}}\right)_n-Het \quad (Ia)$$

| Example No. | R | Az | n | Het | Melting point (°C.) or $n_D^{20}$ |
|---|---|---|---|---|---|
| 30 | 4-Cl-C6H4-O-CH2- | -N(CH=N-CH=)N (imidazolyl) | 1 | 1,3-dioxan-2-yl | 129–30 |
| 31 | biphenyl-4-yl-O-CH2- | imidazolyl | 1 | 1,3-dioxan-2-yl | 138–39 |
| 32 | biphenyl-4-yl-O-CH2- | 1,2,4-triazolyl | 1 | 1,3-dioxan-2-yl | 149 |
| 33 | 4-Cl-C6H4-CH=CH- | 1,2,4-triazolyl | 1 | 1,3-dioxan-2-yl | 147–49 |
| 34 | 4-Cl-C6H4-CH=CH- | 1,2,4-triazolyl | 1 | 1,3-dioxan-2-yl | 152–55 |
| 35 | 4-Cl-C6H4-CH2-CH2- | 1,2,4-triazolyl | 1 | 4-ethyl-1,3-dioxolan-2-yl | viscous oil |
| 36 | 4-Cl-C6H4-CH2-CH2- | 1,2,4-triazolyl | 1 | 4-ethyl-1,3-dioxolan-2-yl | viscous oil |
| 37 | 4-Cl-C6H4-O-CH2- | 1,2,4-triazolyl | 1 | 4-ethyl-1,3-dioxolan-2-yl | 169–72 |
| 38 | 4-Cl-C6H4-O-CH2- | 1,2,4-triazolyl | 1 | 4-ethyl-1,3-dioxolan-2-yl | viscous oil |
| 39 | 4-Cl-C6H4-O-CH2- | 1,2,4-triazolyl | 1 | 1,3-dioxan-2-yl | viscous oil |
| 40 | 4-Cl-C6H4-CH2-CH2- | 1,2,4-triazolyl | 1 | 1,3-dioxan-2-yl | 110–12 |

-continued

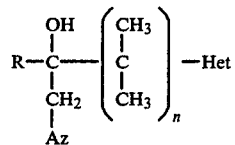
(Ia)

| Example No. | R | Az | n | Het | Melting point (°C.) or $n_D^{20}$ |
|---|---|---|---|---|---|
| 41 | 4-Cl-C6H4-CH2-CH2- | -N(triazole) | 1 | 1,3-dioxane | 117-19 |
| 42 | triazol-1-yl-CH2- | -N(triazole) | 1 | 1,3-dioxolane-CH2-O-(2,4-Cl2-C6H3) | 1.5461 |
| 43 | 4-Cl-C6H4-CH=CH- | -N(triazole) | 1 | 1,3-dioxolane-C2H5 | 80 |
| 44 | 4-Cl-C6H4-CH=CH- | -N(imidazole) | 1 | 1,3-dioxolane-C2H5 | 88-90 |
| 45 | 4-Cl-C6H4-S-CH2- | -N(triazole) | 1 | 1,3-dioxolane | viscous oil |
| 46 | biphenyl-O-CH2- | -N(triazole) | 1 | 1,3-dioxolane-C2H5 | 105 |
| 47 | 2,4-Cl2-C6H3-CH=CH- | -N(imidazole) | 0 | 2,2,5,5-tetramethyl-1,3-dioxane (CH3)2C(CH2O)2C(CH3)2 | viscous oil |
| 48 | 2,4-Cl2-C6H3-CH=CH- | -N(triazole) | 0 | 2,2,5,5-tetramethyl-1,3-dioxane | viscous oil |
| 49 | O | -N(triazole) | 1 | 1,3-dioxolane | viscous oil |
| 50 | O | -N(imidazole) | 1 | 1,3-dioxolane | 100 |

-continued (Ia)

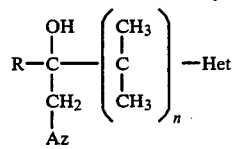

| Example No. | R | Az | n | Het | Melting point (°C.) or $n_D^{20}$ |
|---|---|---|---|---|---|
| 51 | 4-Cl-C6H4-CH2-CH2- (with extra Cl) | triazole (N=N-N) | 1 | dioxolane with C3H7 | viscous oil |
| 52 | 2,4-Cl2-C6H3-CH2-CH2- | imidazole | 1 | dioxolane with C3H7 | 115 |
| 53 | 2,4-Cl2-C6H3-CH2-CH2- | triazole | 1 | dioxolane with C3H7 | viscous oil |
| 54 | 4-Cl-C6H4-CH2CH2- | imidazole | 1 | dioxolane with CH3, x | viscous oil |
| 55 | 2,4-Cl2-C6H3-CH2CH2- | imidazole | 1 | dioxolane with CH3, x | viscous oil |
| 56 | 2-CH3-4-Cl-C6H3-O-CH2- | imidazole | 1 | dioxolane with CH3, x | viscous oil |
| 57 | 2-CH3-4-Cl-C6H3-O-CH2- | imidazole | 1 | dioxolane | 123 |
| 58 | 2-CH3-4-Cl-C6H3-O-CH2- | triazole | 1 | dioxolane | 81 |
| 59 | biphenyl-CH=CH- | imidazole | 1 | 5,5-dimethyl-1,3-dioxane (CH3) | 146 |
| 60 | biphenyl-CH=CH- | triazole | 0 | 5,5-dimethyl-1,3-dioxane (CH3) | 170 |

-continued (Ia)

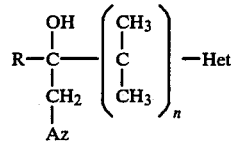

| Example No. | R | Az | n | Het | Melting point (°C.) or $n_D^{20}$ |
|---|---|---|---|---|---|
| 61 | biphenyl-CH$_2$CH$_2$- | 1,2,4-triazol-1-yl | 0 | 5-methyl-1,3-dioxan-5-yl | 98 |
| 62 | biphenyl-CH$_2$CH$_2$- | imidazol-1-yl | 0 | 5-methyl-1,3-dioxan-5-yl | 131 |
| 63 | 4-chloro-2-methylphenoxy-CH$_2$- | 1,2,4-triazol-1-yl | 1 | 2-ethyl-1,3-dioxolan-2-yl | viscous oil |
| 64 | 4-chloro-2-methylphenoxy-CH$_2$- | imidazol-1-yl | 1 | 2-ethyl-1,3-dioxolan-2-yl | viscous oil |
| 65 | 4-chloro-2-methylphenoxy-CH$_2$- | 1,2,4-triazol-1-yl | 1 | 2-ethyl-1,3-dioxolan-2-yl | viscous oil |
| 66 | naphth-1-yloxy-CH$_2$- | imidazol-1-yl | 1 | 1,3-dioxolan-2-yl | 126 |
| 67 | 4-chloro-2-methylphenoxy-CH$_2$- | imidazol-1-yl | 1 | 2-propyl-1,3-dioxolan-2-yl | viscous oil |
| 68 | 4-chlorophenyl- | 1,2,4-triazol-1-yl | 1 | 2-ethyl-1,3-dioxolan-2-yl | viscous oil |
| 69 | 4-chloro-2-methylphenoxy-CH$_2$- | 1,2,4-triazol-1-yl | 1 | 2-propyl-1,3-dioxolan-2-yl | viscous oil |
| 70 | 4-chloro-2-methylphenoxy-CH$_2$- | 1,2,4-triazol-1-yl | 1 | 2-propyl-1,3-dioxolan-2-yl | viscous oil |

-continued $$R-\underset{\underset{Az}{CH_2}}{\overset{\overset{OH}{|}}{C}}\left(\underset{CH_3}{\overset{CH_3}{\overset{|}{C}}}\right)_n-Het \qquad (Ia)$$

| Example No. | R | Az | n | Het | Melting point (°C.) or $n_D^{20}$ |
|---|---|---|---|---|---|
| 71 | 3-methyl-4-(chloromethylphenoxy)methyl (2-Me, 4-Cl-phenyl-O-CH₂–) | 1,2,4-triazol-1-yl (–N, linked via N to C=N–N=) | 1 | 1,3-dioxolan-2-yl with C₃H₇ | viscous oil |
| 72 | naphth-1-yloxymethyl | 1,2,4-triazol-1-yl | 1 | 1,3-dioxolan-2-yl | viscous oil |
| 73 | naphth-1-yloxymethyl | 1,2,4-triazol-1-yl | 0 | 5-methyl-1,3-dioxan-2-yl (CH₃) | 96–98 |
| 74 | naphth-1-yloxymethyl | imidazol-1-yl | 0 | cyclopropyl | 148–151 |
| 75 | 4-biphenylyloxymethyl | 1,2,4-triazol-1-yl | 0 | cyclopropyl | 113–115 |
| 76 | 4-biphenylyloxymethyl | imidazol-1-yl | 0 | cyclopropyl | 169–171 |
| 77 | 4-biphenylyl-CH=CH– | 1,2,4-triazol-1-yl | 1 | 1,3-dioxolan-2-yl with C₂H₅ | viscous oil |
| 78 | 4-biphenylyl-CH=CH– | imidazol-1-yl | 1 | 1,3-dioxolan-2-yl with C₂H₅ | 132–135 |
| 79 | 4-biphenylyl-CH₂-CH₂– | 1,2,4-triazol-1-yl | 1 | 1,3-dioxolan-2-yl with C₂H₅ | viscous oil |

-continued

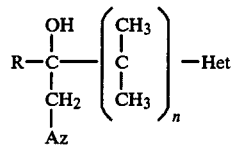
(Ia)

| Example No. | R | Az | n | Het | Melting point (°C.) or $n_D^{20}$ |
|---|---|---|---|---|---|
| 80 | C₆H₅–C₆H₄–CH₂–CH₂– | imidazol-1-yl | 1 | 2-ethyl-1,3-dioxolan-2-yl | viscous oil |
| 81 | 4-Cl–C₆H₄– | imidazol-1-yl | 1 | 2-ethyl-1,3-dioxolan-2-yl | viscous oil |
| 82 | C₆H₅–C₆H₄– | 1,2,4-triazol-1-yl | 1 | 2-ethyl-1,3-dioxolan-2-yl | viscous oil |
| 83 | 4-Cl-2-CH₃–C₆H₃–O–CH₂– | 1,2,4-triazol-1-yl | 1 | 2-methyl-1,3-dioxolan-2-yl | viscous oil |
| 84 | 4-Cl-2-CH₃–C₆H₃–O–CH₂– | imidazol-1-yl | 1 | 2-ethyl-1,3-dioxolan-2-yl | viscous oil |
| 85 | 4-Cl-2-CH₃–C₆H₃–O–CH₂– | 1,2,4-triazol-1-yl | 1 | 2-methyl-1,3-dioxolan-2-yl | viscous oil |
| 86 | 4-Cl-2-CH₃–C₆H₃–O–CH₂– | imidazol-1-yl | 1 | 2-methyl-1,3-dioxolan-2-yl | viscous oil |
| 87 | 3,4-Cl₂–C₆H₃– | 1,2,4-triazol-1-yl | 1 | 1,3-dioxolan-2-yl | viscous oil |
| 88 | 2,4-Cl₂–C₆H₃– | imidazol-1-yl | 1 | 1,3-dioxolan-2-yl | 138 |
| 89 | 4-(CH₃)₃C–C₆H₄– | 1,2,4-triazol-1-yl | 1 | 1,3-dioxolan-2-yl | viscous oil |

-continued $$R-\underset{\underset{Az}{|}}{\overset{\overset{OH}{|}}{\underset{CH_2}{C}}}-\left(\underset{\underset{CH_3}{|}}{\overset{\overset{CH_3}{|}}{C}}\right)_n-Het \qquad (Ia)$$

| Example No. | R | Az | n | Het | Melting point (°C.) or $n_D^{20}$ |
|---|---|---|---|---|---|
| 90 | (CH₃)₃C—C₆H₄— | 1,2,4-triazol-1-yl | 1 | 1,3-dioxolan-2-yl | 164–166 |
| 91 | 3,4-Cl₂—C₆H₃— | 1,2,4-triazol-1-yl | 1 | 2-ethyl-1,3-dioxolan-2-yl | splintery |
| 92 | biphenyl-CH₂—CH₂— | 1,2,4-triazol-1-yl | 1 | 1,3-dioxolan-2-yl | 99–102 |
| 93 | 2,4-Cl₂—C₆H₃—O—CH₂— | 1,2,4-triazol-1-yl | 1 | 1,3-dioxolan-2-yl | 88–90 |
| 94 | biphenyl— | 1,2,4-triazol-1-yl | 1 | 2-methyl-1,3-dioxolan-2-yl | 120 |
| 95 | 4-Br—C₆H₄—S—CH₂— | 1,2,4-triazol-1-yl | 1 | 1,3-dioxolan-2-yl | viscous oil |
| 96 | 2-Cl-4-CF₃—C₆H₃—S—CH₂— | 1,2,4-triazol-1-yl | 1 | 2-ethyl-1,3-dioxolan-2-yl | viscous oil |
| 97 | 4-(n-C₅H₁₁)—C₆H₄—S—CH₂— | 1,2,4-triazol-1-yl | 1 | 2-ethyl-1,3-dioxolan-2-yl | 1,540 |
| 98 | 2,4-Cl₂-5-CH₃—C₆H₂—S—CH₂— | 1,2,4-triazol-1-yl | 1 | 2-ethyl-1,3-dioxolan-2-yl | 137–141 |
| 99 | 3,5-Cl₂-2-CH₃—C₆H₂—S—CH₂— | 1,2,4-triazol-1-yl | 1 | 2-ethyl-1,3-dioxolan-2-yl | 104–107 |

-continued

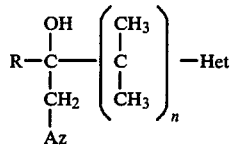

(Ia)

| Example No. | R | Az | n | Het | Melting point (°C.) or $n_D^{20}$ |
|---|---|---|---|---|---|
| 100 | Br—⌬—S—CH₂— | —N(N=N) triazole | 1 | O—CH(C₂H₅)—O (dioxolane) | viscous oil |

NDA = naphthalene-1,5-disulphonic acid

USE EXAMPLES

In the examples which follow the compounds given below are employed as comparative substances:

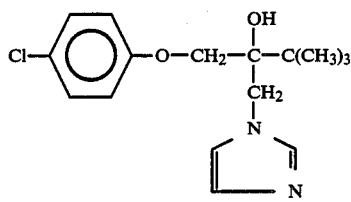

(A)

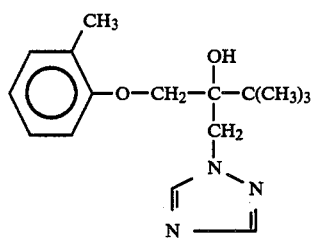

(B)

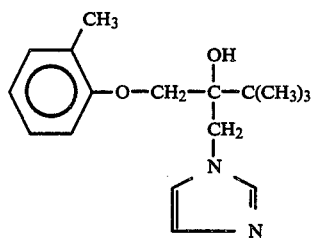

(C)

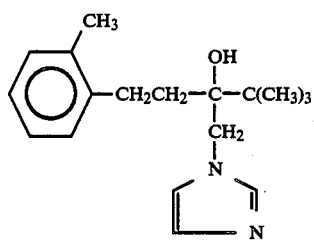

(D)

Example A

Antimycotic in vitro activity
Description of the experiment:
The in vitro tests were carried out in a series dilution test with germ inocula of an average of $5 \times 10^4$ germs/ml of substrate. The nutrient medium was (a) for dermatophytes and moulds: Sabourand's milieu d'epreuve and (b) for yeasts: meat extract/glucose broth.

The incubation temperature was 20° C. and the duration of incubation was 24 to 96 hours in the case of yeasts and 96 hours in the case of dermatophytes and moulds.

In this test, for example, the compounds 3, 5, 7, 8, 9, 10, 11, 12, 13, 14, 15, 16, 19, 20, 21 and 23 according to the invention showed a better antimycotic action than the compounds (A), (B), (C) and (D) which are known from the state of the art.

TABLE A

Antimycotic in vitro activity
MIC values in/ml of nutrient medium

| Active compound | Tricho- phyton mentagr. | Micro- sporum canis | Candida albi- cans | Toru- lopsis glabrata | Asper- gillus fumi- gatus |
|---|---|---|---|---|---|
| (A) (known) | 8 | 16 | 1 | 2 | 32 |
| (B) (known) | 4 | 4 | 32 | >64 | 32 |
| (C) (known) | 32 | — | 32 | >64 | >64 |
| (D) (known) | 8 | 16 | 2 | 16 | 64 |
| Compounds according to Preparation Example | | | | | |
| 3 | <1 | 8 | 8 | 8 | 8 |
| 5 | <1 | <1 | <1 | 8 | 4 |
| 7 | <1 | 2 | <1 | 2 | <1 |
| 8 | <1 | <1 | <1 | 8 | 2 |
| 9 | <1 | 4 | <1 | 8 | 4 |
| 10 | <1 | <1 | <1 | 4 | <1 |
| 11 | <2 | 2 | 2 | 16 | 16 |
| 12 | <1 | 16 | <1 | 32 | 8 |
| 13 | <1 | 16 | 2 | 32 | 32 |
| 14 | <1 | 8 | <1 | 2 | <1 |
| 15 | <1 | 8 | <1 | 4 | 8 |
| 16 | 2 | 16 | <1 | 32 | 32 |
| 19 | <1 | 4 | <1 | 2 | 4 |
| 20 | <1 | <1 | <1 | 2 | 16 |
| 21 | 4 | <1 | <1 | 16 | 32 |
| 23 | 2 | <1 | <1 | 8 | 32 |

Example B

Antimycotic in vivo activity (oral) in candidosis of mice

Description of the experiment

Mice of the SPF-CF₁ type were infected intravenously with $1-2 \times 10^6$ logarithmically growing Candida cells, which are suspended in physiological sodium chloride solution. The animals were treated orally one hour before and seven hours after the infection, with, in each case, 50–100 mg/kg of body weight of the formulations.

Result

Untreated animals died 3 to 6 days after infection. The survival rate on the 6th day after infection was about 5% in the case of untreated control animals.

In this test, for example, the compounds 3, 7, 8, 9, 10, 14, 15, 16, 19, 20, 21, 22, 23 and 26 according to the invention showed a better action than the compounds (A), (B), (C) and (D) which are known from the state of the art.

Explanation of symbols

| | | |
|---|---|---|
| +++++ = | very good action = | 90% survival on the 6th day after infection |
| ++++ = | good action = | 80% survival on the 6th day after infection |
| +++ = | action = | 60% survival on the 6th day after infection |
| ++ = | weak action = | 40% survival on the 6th day after infection |
| + = | trace of an action = | less than 40% survival on the 6th day after infection |
| n.a. = | no action | |

TABLE B

Antimycotic in vivo action (oral) in Candidosis of mice

| Active compound | Action |
|---|---|
| (A) (known) | n.a. |
| (B) (known) | n.a. |
| (C) (known) | n.a. |
| (D) (known) | n.a. |
| Compounds according to preparation examples | |
| 3 | +++ |
| 7 | ++++ |
| 8 | +++ |
| 9 | +++++ |
| 10 | +++ |
| 14 | ++++ |
| 15 | ++++ |
| 16 | ++++ |
| 19 | +++++ |
| 20 | ++++ |
| 21 | +++ |
| 22 | +++++ |
| 23 | +++++ |
| 26 | +++ |

Example C

Antimicrobial in vivo activity (local) in the model of experimental guinea-pig trichophytosis Description of the experiment White mice of the Pirbright-White race were infected, on the shaved, non-scarifed back, with a micro- and macro-eonidia suspension of trichophyton of mentagrophytes.

Beginning on the 3rd day after infection, the animals were treated locally, once daily, with a 15% strength solution of the formulations according to the invention (in dimethylsulphoxide:glycerol=1:4).

Result

In the case of untreated animals, the typical picture of a dermatophytosis, with reddening, scaling and loss of hair until a total integument destruction occurred at the point of infection, developed within 12 days after infection.

In this test, for example, the compounds 7, 8, 9, 10, 14, 19, 20, 21, 22 and 23 according to the invention exhibited an action or a good action.

TABLE C

Antimycotic in vivo activity (local) in the model of experimental guinea-pig trichophytosis

| Active compound according to preparation Example | Action |
|---|---|
| 7 | +++ |
| 8 | ++ |
| 9 | ++++ |
| 10 | ++++ |
| 14 | ++++ |
| 19 | +++ |
| 20 | ++ |
| 21 | ++ |
| 22 | +++ |
| 23 | ++ |

+++++ = very good action = no sign of infection on the 12th to 15th day after infection
++++ = good action = slight reddening, isolated scales
+++ = action = reddening, scales, no loss of hair
++ = weak action = reddening, scaling, loss of hair
+ = trace of an action = loss of hair over extensive area, inflammatory skin reaction

Example D/formulations

1. Solution

| | |
|---|---|
| Active compound according to formula (I): | 10 g |
| Alcohol, pure (96% strength): | 300 g |
| Isopropyl myristate: | 526 g |
| | 836 g |

2. Cream

| | |
|---|---|
| Active compound according to formula (I): | 10 g |
| Arlacel 60: (sorbitane monostearate) | 20 g |
| Tween 60: (polyoxyethylene-20 sorbitane monostearate) | 15 g |
| Spermaceti, synthetic: (mixture of esters of saturated $C_{14}$–$C_{18}$ fatty acids and $C_{14}$–$C_{18}$ fatty alcohols) | 30 g |
| Lanette O: (mixture of cetyl alcohol and stearyl alcohol) | 100 g |
| Ethanol G: (2-octyl-dodecanol) | 135 g |
| Benzyl alcohol: | 10 g |
| Water, demineralised | 680 g |
| | 1,000 g |

What is claimed is:

1. A pharmaceutical composition containing as an antimycotic agent, an antimycotically effective amount of a compound of the formula

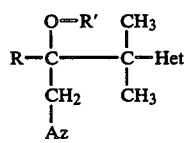

in which

Az represents 1,2,4-triazol-1-yl, 1,2,4-triazol-4-yl or imidazol-1-yl,

Het represents dioxolan-2-yl or 1,3-dioxanyl, each of which is optionally substituted by identical or different substituents selected from the group consisting of alkyl with 1 to 4 carbon atoms, and phenyl and phenoxyalkyl with 1 to 4 carbon atoms in the alkyl part, each of which is optionally substituted on the phenyl by identical or different substituents selected from the group consisting of halogen, alkyl with 1 to 4 carbon atoms, alkoxy and alkylthio with in each case 1 or 2 carbon atoms and halogenoalkyl, halogenoalkoxy and halogenoalkylthio with in each case 1 or 2 carbon atoms and 1 to 5 identical or different halogen atoms;

R represents straight-chain or branched alkyl with 1 to 7 carbon atoms, or phenyl, phenylalkyl with 1 to 4 carbon atoms in the alkyl part, phenoxy- or phenylthio-alkyl with in each case 1 to 4 carbon atoms in the alkyl part or phenylethenyl, each of which is optionally substituted on the phenyl by identical or different substituents selected from the group consisting of halogen, alkyl with 1 to 4 carbon atoms, alkoxy and alkylthio with in each case 1 or 2 carbon atoms, nitro, halogenoalkyl, halogenoalkoxy and halogenoalkylthio with in each case 1 or 2 carbon atoms and 1 to 5 identical or different halogen atoms, hydroximinoalkyl with 1 to 4 carbon atoms, alkoximinoalkyl with 1 to 4 carbon atoms in each alkyl part, and phenyl, phenoxy, benzyl and benzyloxy, each of which is optionally substituted by halogen or alkyl with 1 or 2 carbon atoms; or R represents cycloalkyl with 5 to 7 carbon atoms, which is in each case optionally monosubstituted or polysubstituted by identical or different alkyl radicals with 1 to 4 carbon atoms, or cycloalkyl-methyl or -ethyl with 5 to 7 carbon atoms in the cycloalkyl part, or cyclohexylethenyl, or, alkenyl with 2 to 6 carbon atoms, 2-furyl, naphthyloxymethyl, 1,2,4-triazol-1-yl-methyl, 1,2,4-triazol-4-yl-methyl, imidazol-1-yl-methyl or pyrazol-1-yl-methyl, R' represents hydrogen, alkyl which has 1 to 4 carbon atoms and is optionally substituted by phenyl, it being possible for the phenyl radical to be substituted by the substituents on phenyl mentioned under R, or alkenyl with 2 to 4 carbon atoms, or an addition product thereof with an acid or metal salt an an inert pharmaceutical carrier.

2. A pharmaceutical composition containing as an antimycotic, an antimycotically effective amount of a compound of the formula

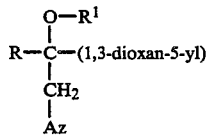

in which

Az represents 1,2,4-triazol-1-yl, 1,2,4-triazol-4-yl or imidazol-1-yl, the 1,3-dioxolan-5-yl is optionally substituted by identical or different substituents selected from the group consisting of alkyl with 1 to 4 carbon atoms, and phenyl and phenoxyalkyl with 1 to 4 carbon atoms in the alkyl part, each of which is optionally substituted on the phenyl by identical or different substituents selected from the group consisting of halogen, alkyl with 1 to 4 carbon atoms, alkoxy and alkylthio with in each case 1 or 2 carbon atoms and halogenoalkyl, halogenoalkoxy and halogenoalkylthio with in each case 1 or 2 carbon atoms and 1 to 5 identical or different halogen atoms;

R represents straight-chain or branched alkyl with 1 to 7 carbon atoms, or phenyl, phenylalkyl with 1 to 4 carbon atoms in the alkyl part, phenoxy- or phenylthio-alkyl with in each case 1 to 4 carbon atoms in the alkyl part or phenylethenyl each of which is optionally substituted on the phenyl by identical or different substituents selected from the group consisting of halogen, alkyl with 1 to 4 carbon atoms, alkoxy and alkylthio with in each case 1 or 2 carbon atoms, nitro, halogen alkyl, halogenoalkoxy and halogenoalkylthio with in each case 1 or 2 carbon atoms and 1 to 5 identical or different halogen atoms, hydroximinoalkyl with 1 to 4 carbon atoms, alkoximinoalkyl with 1 to 4 carbon atoms in each alkyl part, and phenyl, phenoxy, benzyl and benzyloxy, each of which is optionally substituted by halogen or alkyl with 1 or 2 carbon atoms; or R represents cycloalkyl with 5 to 7 carbon atoms, which is in each case optionally monosubstituted or polysubstituted by identical or different alkyl radicals with 1 to 4 carbon atoms, or cycloalkyl-methyl or -ethyl with 5 to 7 carbon atoms in the cycloalkyl part, or cyclohexylethenyl, or, alkenyl with 2 to 6 carbon atoms, 2-furyl, naphthyloxymethyl, 1,2,4-triazol-1-yl-methyl, 1,2,4-triazol-4-yl-methyl, imidazol-1-yl-methyl or pyrazol-1-yl-methyl, R' represents hydrogen, alkyl which has 1 to 4 carbon atoms and is optionally substituted by phenyl, it being possible for the phenyl radical to be substituted by the substituents on phenyl mentioned under R, or alkenyl with 2 to 4 carbon atoms, or an addition product thereof with an acid or metal salt and an inert pharmaceutical carrier.

3. A pharmaceutical composition according to claim 1 in which

Het represents dioxolan-2-yl, or 1,3-dioxan-2-yl, each of which is optionally monosubstituted to trisubstituted by identical or different substituents selected from the group consisting of methyl, ethyl, n-propyl, isopropyl, and phenyl and phenoxymethyl, each of which is optionally monosubstituted to trisubstituted by identical or different substituents selected from the group consisting of fluorine, chlorine, methyl, trifluoromethyl or trifluoromethoxy; R represents tert.-butyl, trimethyl-propyl, tetramethylpropyl, and phenyl, benzyl, phenethyl, phenoxymethyl, phenylthiomethyl or phenethenyl, each of which is optionally monosubstituted to trisubstituted by identical or different substituents, selected from the group consisting of phenyl substituents being selected from the group consisting of fluorine, chlorine, methyl, trifluoromethyl, trifluoromethoxy, trifluoromethylthio, hydroximinomethyl, 1-hydroxyiminoethyl, methoximinomethyl and 1-methoximinoethyl, and phenyl, phenoxy or benzyl and benzyloxy, each of which is optionally substituted by chlorine and/or methyl; R furthermore represents cyclohexyl, cyclohexylmethyl, cyclohexylethyl or cyclohexylethenyl, each of which is optionally monosubstituted or disubstituted by identical or different substituents selected from the group consisting of methyl, ethyl, or isopropyl; or R represents allyl, dimethylpropenyl, 2-furyl, naphthyloxymethyl, 1,2,4-triazol-1-yl-methyl, 1,2,4-triazol-4-yl-methyl, imidazol-1-yl-methyl or pyrazol-1-yl-methyl, R' represents hydrogen, methyl, 4-chlorobenzyl or allyl and an inert pharmaceutical carrier.

4. A pharmaceutical composition according to claim 2, in which the 1,3-dioxan-5-yl is optionally monosubstituted to trisubstituted by identical or different substituents selected from the group consisting of methyl, ethyl, n-propyl, isopropyl, and phenyl and phenoxymethyl, each of which is optionally monosubstituted to trisubstituted by identical or different substituents selected from the group consisting of fluorine, chlorine, methyl, trifluoromethyl or trifluoromethoxy, R represents tert.-butyl, trimethylpropyl, tetramethylpropyl, and phenyl, benzyl, phenethyl, phenoxymethyl, phenylthiomethyl or phenethenyl, each of which is optionally monosubstituted to trisubstituted by identical or different substituents, selected from the group consisting of phenyl substituents being selected from the group consisting of fluorine, chlorine, methyl, trifluoromethyl, trifluoromethoxy, trifluoromethylthio, hydroximinomethyl, 1-hydroxyiminoethyl, methoximinomethyl and 1-methoximinoethyl, and phenyl, phenoxy or benzyl and benzyloxy, each of which is optionally substituted by chlorine and/or methyl;

R furthermore represents cyclohexyl, cyclohexylmethyl, cyclohexylethyl or cyclohexylethenyl, each of which is optionally monosubstituted or di-substituted by identical or different substituents selected from the group consisting of methyl, ethyl, or isopropyl; or R represents allyl, dimethylpropenyl, 2-furyl, naphthyloxymethyl, 1,2,4-triazol-1-yl-methyl, 1,2,4-triazol-4-yl-methyl, imidazol-1-yl-methyl or pyrazol-1-yl-methyl, R' represents hydrogen, methyl, 4-chlorobenzyl or allyl or an acid addition salt or metal salt complex; and an inert pharmaceutical carrier.

5. A medicament, in dosage unit form comprising an antimycotically effective amount of a compound of claim 1 and an inert pharmaceutical carrier.

6. A medicament of claim 5 in the form of tablets, capsules, pills, dragees, ampoules or suppositories.

7. A medicament, in dosage unit form comprising an antimycotically effective amount of a compound of claim 4 and an inert pharmaceutical carrier.

8. A medicament of claim 7 in the form of tablets, capsules, pills, dragees, ampoules or suppositories.

9. A pharmaceutical composition of claim 3 wherein the antimycotic agent is 2-(4-chlorophenyl)-3-(1,3-dioxolan-2-yl)-3-methyl-1-(1,2,4-triazol-1-yl)-2-butanol.

10. A pharmaceutical composition of claim 3 wherein the antimycotic agent is 1-(4-chlorophenyl)-4-(1,3-dioxolan-2-yl)-4-methyl-3-(1,2,4-triazol-1-yl-methyl)-1-penten-3-ol.

11. A pharmaceutical composition of claim 3 wherein the antimycotic agent is 1-(4-biphenylyloxy)-3-(1,3-dioxolan-2-yl)-3-methyl-2-(1,2,4-triazol-1-yl-methyl)-2-butanol.

12. A pharmaceutical composition of claim 3 wherein the antimycotic agent is 1-(4-chlorophenoxy)-3-(4-ethyl-1,3-dioxolan-2-yl)-3-methyl-2-(1,2,4-triazol-1-yl-methyl)-2-butanol-1,5-naphthalenedisulfonate.

13. A pharmaceutical composition of claim 3 wherein the antimycotic agent is 1-(4-chlorophenyl)-4-(4-ethyl-1,3-dioxolan-2-yl)-4-methyl-3-(1,2,4-triazol-1-yl-methyl)-1-penten-3-ol.

14. A pharmaceutical composition of claim 3 wherein the antimycotic agent is 1-(4-chlorophenyl)-3-(imidazol-1-yl-methyl)-4-(4-methyl-1,3-dioxolan-2-yl)-4-methyl-3-pentanol.

15. A pharmaceutical composition of claim 2 wherein the antimycotic agent is 1-(4-chlorophenyl)-3-(5-methyl-1,3-dioxan-5-yl)-4-(1,2,4-triazol-1-yl)-3-butanol.

16. A method of combatting mycoses in warm-blooded animals which comprises administering to the animals an antimycotically effective amount of an active compound of claim 1 either alone, in admixture with a diluent or in the form of a medicament.

17. A method of combatting mycoses in warm-blooded animals which comprises administering to the animals an antimycotically effective amount of an active compound of claim 2 either alone, in admixture with a diluent or in the form of a medicament.

18. A method of claim 16 in which the active compound is administered in an amount of about 10 to about 300 mg/kg body weight per day.

19. A method according to claim 18 in which the active compound is administered orally or parenterally.

20. A method of claim 17 in which the active compound is administered in an amount of about 10 to about 300 mg/kg body weight per day.

21. A method according to claim 20 in which the active compound is administered orally or parenterally.

* * * * *